(12) United States Patent
Bokrantz et al.

(10) Patent No.: US 12,370,375 B2
(45) Date of Patent: Jul. 29, 2025

(54) DYNAMIC ESTIMATION OF A BIOLOGICAL EFFECT OF A VARIABLE COMPOSITION OF NON-PHOTON RADIATION

(71) Applicant: RaySearch Laboratories AB (Publ), Stockholm (SE)

(72) Inventors: Rasmus Bokrantz, Enebyberg (SE); Lars Glimelius, Stockholm (SE)

(73) Assignee: Raysearch Laboratories AB (publ), Stockholm (SE)

( * ) Notice: Subject to any disclaimer, the term of this patent is extended or adjusted under 35 U.S.C. 154(b) by 413 days.

(21) Appl. No.: 18/001,297

(22) PCT Filed: Jun. 14, 2021

(86) PCT No.: PCT/EP2021/065970
§ 371 (c)(1),
(2) Date: Dec. 9, 2022

(87) PCT Pub. No.: WO2021/259690
PCT Pub. Date: Dec. 30, 2021

(65) Prior Publication Data
US 2023/0233876 A1    Jul. 27, 2023

(30) Foreign Application Priority Data
Jun. 23, 2020   (EP) .................... 20181570

(51) Int. Cl.
*A61N 5/10*   (2006.01)
*G16H 20/40*   (2018.01)
(52) U.S. Cl.
CPC ............ *A61N 5/103* (2013.01); *G16H 20/40* (2018.01); *A61N 2005/1087* (2013.01)
(58) Field of Classification Search
CPC . A61N 5/103; A61N 2005/1087; G16H 20/40
See application file for complete search history.

(56) References Cited

U.S. PATENT DOCUMENTS

2009/0060130 A1   3/2009  Wilkens et al.
2020/0298025 A1*  9/2020  Cooley, III ......... A61N 5/1045

FOREIGN PATENT DOCUMENTS

CN     106902478 B    6/2019
EP       3581241 A1  12/2019
WO    2012032609 A1   3/2012

OTHER PUBLICATIONS

Carabe-Fernandez, A. et al., "The incorporation of the concept of minimum RBE (RBEmin) into the linear-quadratic model and the potential for improved radiobiological analysis of high-LET treatments", Int. J. Radiat. Biol. (2007), vol. 83, pp. 27-39 [doi:10.1080/09553000601087176].

(Continued)

*Primary Examiner* — David P Porta
*Assistant Examiner* — Mamadou Faye
(74) *Attorney, Agent, or Firm* — Noréns Patentbyrå AB

(57) ABSTRACT

A method for dynamically estimating a biological effect of a variable combination of non-photon radiation in accordance with a relative biological effectiveness, RBE, model including at least one biological effect multiplier $\delta(T,E)$ which depends on particle type T and/or particle energy E, the method comprising:

obtaining one or more non-photon radiation contributions $D^{(i)}(T,E)$, $1 \leq i \leq N$, at least one of said contributions including multiple particle types and/or multiple particle energies;

storing per-contribution dose-weighted averages $\bar{\delta}^{(i)}$, $1 \leq i \leq N$, of said at least one biological effect multiplier with respect to each of the one or more contributions; and in response to obtaining an assignment $\Pi$ of the combination, the assignment being in terms of non-negative coefficients $k_1, k_2, \ldots, k_N \geq 0$ to be applied to the one or more contributions, determining a biological effect (Continued)

of the combination, including computing a combined dose-weighted average $\bar{\delta}^{II}$ of said at least one biological effect multiplier on the basis of the stored per-contribution dose-weighted averages.

18 Claims, 2 Drawing Sheets

(56) References Cited

OTHER PUBLICATIONS

Chen, Y et al., "Empirical model estimation of relative biological effectiveness for proton beam therapy", Radiat. Prot. Dosim. (2012), vol. 149, pp. 116-123 [doi: 10.1093/rpd/ncr218].

Hawkins, R., B. "A microdosimetric-kinetic model for the effect of non-Poisson distribution of lethal lesions on the variation of RBE with LET", Radiat. Res. (2003), vol. 160, pp. 61-69 [doi:10.1667/RR3010].

Krämer, M. et al., "Rapid calculation of biological effects in ion radiotherapy", Phys. Med. Biol. (2006), vol. 51, pp. 1959-1970 [doi:10.1088/0031-9155/51/8/001].

McNamara, A., L. et al., "A phenomenological relative biological effectiveness (RBE) model for proton therapy based on all published in vitro cell survival data", Phys. Med. Biol. (2015), vol. 60, pp. 8399-8416 [doi:10.1088/0031-9155/60/21/8399].

Scholz, M. et al., "Computation of cell survival in heavy ion beams for therapy. The model and its approximation", Radiat. Environ. Biophys. (1997), vol. 36, pp. 59-66 [doi:10.1007/s004110050055]).

Wedenberg, M. et al., "A model for the relative biological effectiveness of protons: The tissue specific parameter $\alpha/\beta$ of photons is a predictor for the sensitivity to LET changes", Acta Oncologica (2013), vol. 52, pp. 580-588 [doi:10.3109/0284186X.2012.705892].

Zaider, M et al., "The synergistic effects of different radiations", Radiat. Res. (1980), vol. 83, pp. 732-739 [doi:10.2307/3575352].

International Search Report & Written Opinion, European Patent Office, Sep. 17, 2021, Rijswijk, Netherlands.

* cited by examiner

DYNAMIC ESTIMATION OF A BIOLOGICAL EFFECT OF A VARIABLE COMPOSITION OF NON-PHOTON RADIATION

TECHNICAL FIELD

The present disclosure relates to the field of radiation therapy and in particular to methods and devices for estimating, in accordance with a relative biological effectiveness (RBE) model, a biological effect of a variable composition of non-photon radiation.

BACKGROUND

Non-photon radiation therapy may utilize ion radiation, such as protons, helium or carbon ions. According to common practice within the subfield of radiation therapy, prescriptions, clinical goals and treatment planning protocols may include specifications in terms of equivalent dose. Equivalent dose of a non-photon radiation is biologically equivalent to a reference radiation, such as photon radiation, in which case the terms photon-equivalent dose or photon dose equivalent may be used. The equivalent dose is computed from the physical absorbed dose using the relative biological effectiveness (RBE) of the radiation used, defined as the ratio of the doses required to cause the same level of biological effect. The term RBE factor is used to signify the conversion factor between physical dose and equivalent dose:

equivalent dose=RBE factor×physical dose.

Alternatively, an RBE model may provide an equivalent dose, from which the RBE factor can be calculated as the ratio of the equivalent dose to the physical dose. The RBE model may for example provide the biological effect as a function of the physical dose of the non-photon radiation. Starting from the biological effect, the equivalent dose is found by a simple calculation involving radiobiological parameters of the reference radiation. A commonly used measure of the biological effect is the negative logarithm of cell survival S, and the relevant radiobiological parameters for a photon reference are frequently denoted $\alpha_X$, $\beta_X$ in the literature. Accordingly, the equivalent dose and the biological effect are in a one-to-one relationship for a given choice of reference radiation.

An RBE may be connected with a specific radiobiological model, which has been derived from physical and physiological considerations and possibly validated or refined experimentally. Depending on the underlying radiobiological model, the RBE factor may vary, for example, with respect to the magnitude of the physical dose or with respect to the radiobiological properties of the irradiated tissue. An RBE factor that depends on the physical dose will establish a non-linear relationship between physical dose and equivalent dose. For example, an RBE factor proportional to the $(p-1)^{th}$ power of the physical dose, for some real p>0, will cause the equivalent dose to depend on the $p^{th}$ power of the physical dose. For proton treatment, a widely used RBE factor is the so-called 1.1 model, according to which the biological effectiveness of protons exceeds the effectiveness of photons by 10 percent regardless of the dose and other factors. It is known that the 1.1 model underestimates the dose at the distal end of a proton field. This and other effects may be taken care of by more elaborate RBE models, including those by the authors Carabe, Chen & Ahmad, Krämer & Scholz, McNamara and Wedenberg.

A treatment plan Π may be a linear combination, in particular a convex combination, of two or more base plans $P_1, P_2, \ldots, P_N$ which is formed using coefficients $k_1, k_2, \ldots, k_N \geq 0$. The base plans may have been obtained by multi-criteria optimization (MCO), so that they correspond to different weighting of the different objective constituents, which the user can explore to find a suitable tradeoff between the competing goals; each goal may represent a particular desirable of the treatment, such as high tumor lethality, low exposure of organs-at-risk etc. On this basis, the user may proceed iteratively by initially assigning a set of coefficient values, evaluating the resulting linear combination—a "navigated plan"—, assigning an improved set of coefficient values, evaluating the new navigated plan etc. until a satisfactory treatment plan has been obtained. A treatment planning procedure of this type can be likened to a feedback loop where the coefficient values are the inputs, the evaluated properties are the outputs, and the treatment planner's heuristics and experience form the control law. It is generally desirable for each iteration to be computationally lean, so that treatment planners do not stop their attempts to refine and improve too early. Especially a human treatment planner may be sensitive to the duration of the update interval.

Because many biological effects of radiation are of a nonlinear character, as explained above, the upscaling or downscaling of a mixed radiation field may consume significant processing resources too. The search for a better or best scaling factor should not be interrupted prematurely as a result of tedious iterations.

CN106902478A discloses a method for assessing biological effects in systematized radiotherapy. In the method, microscopic effects (double-strand breaks) are superimposed to obtain a total cell damage $\Delta_i$, which is applied as an initial condition to a system of ordinary differential equations (ODEs). The ODE system reflects the two-lesion kinetic (TLK) radiobiological model, and its solution corresponds to a biological effect predicted by this model. If the energy spectrum D(E) of the physical dose changes, CN106902478A's method has to be executed anew from the calculation of the total cell damage $\Delta_i$ onwards.

Currently there is a need for more computationally efficient ways of evaluating the biological effect of a combination of mixed non-photon radiation fields, with an option of speedy re-evaluation when the combination is varied as a result of navigation. This need is equally valid for the problem of scaling a mixed non-photon radiation field.

SUMMARY

One objective of the invention is to propose improved methods and devices for dynamically estimating a biological effect of a variable combination of non-photon radiation in accordance with an RBE model. It is a particular objective to estimate a macroscopic biological effect of the variable combination of non-photon radiation. Another objective is to propose improved methods and devices for dynamically estimating how a biological effect varies during beam mixing. These and other objectives are addressed by the invention as defined by the independent claims.

In a first aspect, there is provided a method for dynamically estimating a biological effect of a variable combination of non-photon radiation in accordance with an RBE model including at least one biological effect multiplier $\delta(T,E)$ which depends on particle type T and/or particle energy E. According to the method, one or more non-photon radiation contributions $D^{(i)}(T,E)$, $1 \leq i \leq N$, are obtained. In at least one voxel or volume, at least one of these contributions includes multiple particle types T and/or multiple particle energies E. A particle type may be characterized by the mass or charge of the particle. Even in a treatment plan ordering irradiation with a single particle type and a single energy layer, multiple particle types and/or particle energies may arise as a result of fragmentation, energy loss in tissue or the like. Even where the combination includes a single contribution, the scaling problem is non-trivial due to the presence of multiple particle types and/or particle energies, as detailed below.

Once the contribution (N=1) or contributions (N≥2) have been obtained, per-contribution dose-weighted averages $\bar{\delta}^{(i)}$, $1 \leq i \leq N$, of said at least one biological effect multiplier with respect to each of the one or more contributions are stored. The per-contribution dose-weighted averages can be computed as part of the method or received from another source. A dose-weighted average for a contribution can be computed by averaging the biological effect multiplier using the contribution's dose as weights, which may include summing over T and E and normalizing by the contribution's total dose.

The next step of the method is performed responsively. More precisely, when an assignment Π of the combination is obtained, a biological effect of the combination is determined. It is understood that the assignment is expressed in terms of non-negative coefficients $k_1, k_2, \ldots, k_N \geq 0$ to be applied to the one or more contributions in order to combine or interpolate the contributions. The biological effect of the combination may be determined, in part, by computing a combined dose-weighted average $\bar{\delta}^{\Pi}$ of said at least one biological effect multiplier on the basis of the stored per-contribution dose-weighted averages $\bar{\delta}^{\Pi}$. The total physical dose is then multiplied by the combined dose-weighted average of the biological effect multiplier. If the RBE model includes several terms with a respective biological effect multiplier, the combined dose-weighted averaging is performed for each of these.

The method may output the biological effect as a value pertaining to a location x being a point in space or a volume (region) of space. Alternatively, multiple biological effect values for different positions can be output, forming a list, table or function of spatial coordinates.

This aspect of the invention provides a dynamic estimation since it accounts for the variability of the combination in the sense that, when an assignment of the combination is obtained, the biological effect is computed from the stored per-contribution dose-weighted averages $\bar{\delta}^{(i)}$, $1 \leq i \leq N$. When a new assignment is obtained, the biological effect is recomputed from the same stored per-contribution dose-weighted averages. This approach is efficient as it avoids repeating earlier parts of the computation but instead reuses intermediate results of these earlier parts. When put at the disposal of treatment planning, it allows more iterations to be performed in a given amount of time, and thereby contributes to raising the quality of the final combined treatment plan.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

In a second aspect, the invention provides a treatment planning system implementing the above method. In particular, the treatment planning system may comprise an interface configured to receive one or more non-photon radiation contributions $D^{(i)}(T,E)$, $1 \leq i \geq N$, and dynamic assignments Π of the combination in terms of non-negative coefficients $k_1, k_2, \ldots, k_N \geq 0$. The treatment planning system may further comprise a memory configured to store per-contribution dose-weighted averages $\bar{\delta}^{(i)}$, $1 \leq i \leq N$, of said at least one biological effect multiplier and processing circuitry configured to determine, for each received dynamic assignment Π of the combination, a biological effect of the combination.

The invention furthermore provides a computer program with instructions for causing a computer, or said treatment planning system in particular, to carry out the above method. The computer program may be stored or distributed on a data carrier. As used herein, a "data carrier" may be a transitory data carrier, such as modulated electromagnetic or optical waves, or a non-transitory data carrier. Non-transitory data carriers include volatile and non-volatile memories, such as permanent and non-permanent storages of magnetic, optical or solid-state type. Still within the scope of "data carrier", such memories may be fixedly mounted or portable.

BRIEF DESCRIPTION OF THE DRAWINGS

Aspects and embodiments are now described, by way of example, with reference to the accompanying drawings, on which.

DETAILED DESCRIPTION

The aspects of the present disclosure will now be described more fully with reference to the accompanying drawings, on which certain embodiments of the invention are shown. The invention may, however, be embodied in many different forms and the embodiments should not be construed as limiting; rather, they are provided by way of example so that this disclosure will be thorough and complete, and to fully convey the scope of all aspects of invention to those skilled in the art.

Figure 3:
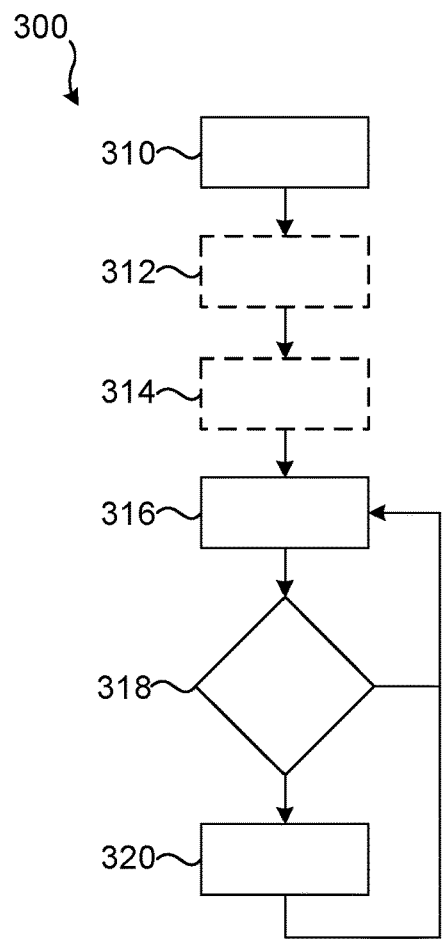
FIG. 3 is a flowchart of a method according to an embodiment.

FIG. 3 is a flowchart of a method 300 for dynamically estimating a biological effect of a treatment plan specifying a non-photon irradiation of a patient, wherein the treatment plan is a combination of non-photon radiation contributions. The non-photon radiation may for example be radiation by ions or protons.

Figure 5:
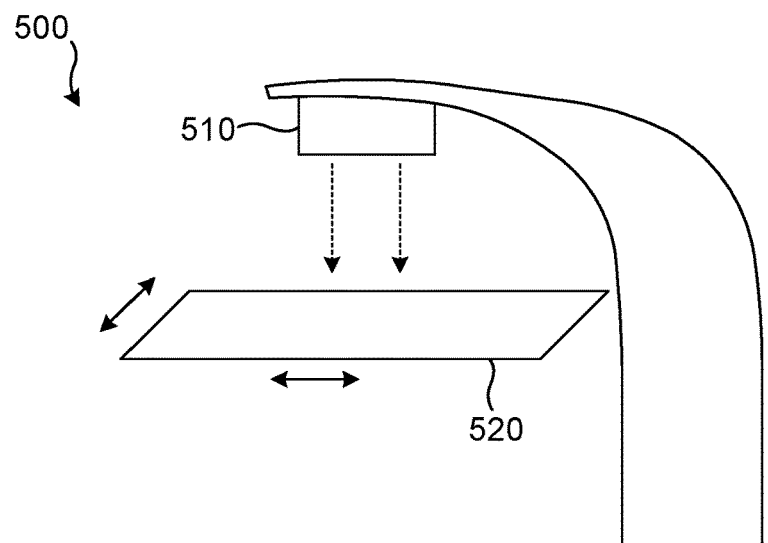
FIG. 5 shows a radiation delivery system for executing a treatment plan.

The treatment plan may be executed by a radiation delivery system 500. As shown in FIG. 5, such system may include a gantry 510 with a radiation source, and a couch 520, which a patient rests on and is fixated to during the treatment. Rotatory and/or translational relative movement between the gantry 510 and couch 520 is possible. In particular, the gantry 510 may be rotatable with respect to one or two axes; and the couch 520 may be rotatable round a vertical axis and translatable in at least one dimension. This allows a multitude of irradiation angles and positions (or incidence directions), as may be described by a corresponding plurality of spots. The treatment plan may specify fluence and/or particle energy values for all or some of the available spots.

The biological effect is to be computed in accordance with a relative biological effectiveness (RBE) model including at least one biological effect multiplier $\delta(T,E)$ which depends on particle type T and/or particle energy E. The biological effect multiplier may further be associated with a value of a characteristic power $p>0$. For particle type T and particle energy E, the biological effect multiplier corresponds to a contribution to the biological effect $-\ln S$ which is equal to $\delta(T,E)\,D(T,E)^p$. For a mixed dose, the total contribution is given by $$\sum_{T,E} \delta(T,E)D(T,E)^p,$$

where the notation $\Sigma_{T,E} \ldots$ is shorthand for summing over all (T,E) pairs for which the dose $D(T,E)>0$. The formalism with biological effect multipliers is useful for representing macroscopic biological effects, e.g., in beam mixing, but may not be sufficient for micro- or nanodosimetric calculations.

An RBE model may be expressed as an RBE factor which is a linear combination of one or more biological effect multipliers. Within the scope of the present invention, an RBE model may be:
- a local effect model (LEM) (see for example the early version described in Scholz et al., "Computation of cell survival in heavy ion beams for therapy. The model and its approximation", *Radiat. Environ. Biophys.* (1997), vol. 36, pp. 59-66 [doi: 10.1007/s004110050055]),
- a microdosimetric-kinetic model (MKM) (see for example Hawkins, "A microdosimetric-kinetic model for the effect of non-Poisson distribution of lethal lesions on the variation of RBE with LET", *Radiat. Res.* (2003), vol. 160, pp. 61-69 [doi: 10.1667/RR3010]).

An LEM by Krämer and Scholz (see Krämer et al., "Rapid calculation of biological effects in ion radiotherapy", *Phys. Med. Biol.* (2006), vol. 51, pp. 1959-1970 [doi:10.1088/0031-9155/51/8/001]) quantifies the biological effect of dose $D(T,E)$ as $$-\ln S = \begin{cases} (\beta(T,E)D(T,E)+\alpha(T,E))D(T,E), & D(T,E) \le D_{cut} \\ (\beta(T,E)D_{cut}+\alpha(T,E))D_{cut}+(D(T,E)-D_{cut})s_{max}, & D(T,E) > D_{cuL} \end{cases}$$

where parameters $\alpha(T,E)$, $\beta(T,E)$, $D_{cut}$ and $s_{max}$ are independent of the macroscopic dose. Hence, the parameters can be applied without modification to any treatment plan. The biological effect $-\ln S$ can be converted into equivalent dose $D_{bio}$ using the following relation:

$$D_{bio} = \begin{cases} \sqrt{-\ln S/\beta_X + (\alpha_X/2\beta_X)^2} - (\alpha_X/2\beta_X), & -\ln S \le -\ln S_{cut} \\ (-\ln S + \ln S_{cut})/s_{max} + D_{cut}, & -\ln S > -\ln S_{cut} \end{cases}$$

In this model, it is notable that the expression $\beta(T,E)D(T,E)+\alpha(T,E)$ includes one multiplier $\alpha$, which is constant with respect to dose, and one multiplier $\beta$, which varies linearly with the dose. Accordingly, the part which is proportional to $\alpha$ will cause the biological effect to depend on the first power of the physical dose (p=1, with the notation introduced above), while the part proportional to $\beta$ will provide a quadratic dependence on the physical dose (p=2). The quantity p will be referred to herein as the characteristic power of the biological effect multiplier. The present disclosure does not disclaim the special case without a modeled cutoff behavior, i.e., notionally setting $D_{cut}=\infty$.

The biological effect according to the MKM may be expressed as follows:

$$-\ln S=(\alpha_0(T,E)+\beta z_{1D}^*(T,E))D(T,E)+\beta(D(T,E))^2,$$

The characteristic power is p=1 for both $\alpha_0(T,E)$ and $z_{1D}^*(T,E)$. Since $\beta$ is constant with respect to different radiation types according to a current version of MKM, it may be applied directly to the total dose.

Further, the RBE factors may be in accordance with one or more phenomenologically based parameterizations of a linear energy transfer (LET) model, such as:
- a Carabe model (see for example Carabe-Fernandez et al., "The incorporation of the concept of minimum RBE (RBEmin) into the linear-quadratic model and the potential for improved radiobiological analysis of high-LET treatments", *Int. J. Radiat. Biol.* (2007), vol. 83, pp. 27-39 [doi: 10.1080/09553000601087176]),
- a Chen & Ahmad model (see for example Chen et al., "Empirical model estimation of relative biological effectiveness for proton beam therapy", *Radiat. Prot. Dosim.* (2012), vol. 149, pp. 116-123 [doi: 10.1093/rpd/ncr218]),
- a McNamara model (see for example McNamara et al., "A phenomenological relative biological effectiveness (RBE) model for proton therapy based on all published in vitro cell survival data", *Phys. Med. Biol.* (2015), vol. 60, pp. 8399-8416 [doi: 10.1088/0031-9155/60/21/8399]),
- a Wedenberg model (see for example Wedenberg et al., "A model for the relative biological effectiveness of protons: The tissue specific parameter $\alpha/\beta$ of photons is a predictor for the sensitivity to LET changes", *Acta Oncologica* (2013), vol. 52, pp. 580-588 [doi: 10.3109/0284186X.2012.705892]).

In this disclosure, a named RBE model includes not only the cited disclosure by the named author but also further developments by same or other authors, as well as quantitative and qualitative variations of the disclosed model.

A still further option is to use external software which inputs a dose of specified particle type T and particle energy E and outputs a value of a biological effect multiplier, an RBE factor, an equivalent dose or a biological effect. The software may be provided as source code which is caused to be executed by the method 300. Alternatively, repeated calls to a local software library are made during execution of the method 300. Further alternatively, and especially if low latency can be ensured, calls are made to a web application programming interface (API). The software is external in the sense of being opaque to the treatment planner, i.e., it returns an output (biological effect) for every admissible input (physical dose) but the treatment planner need not be aware of the RBE model that it implements or other considerations underlying the software.

Figure 4:
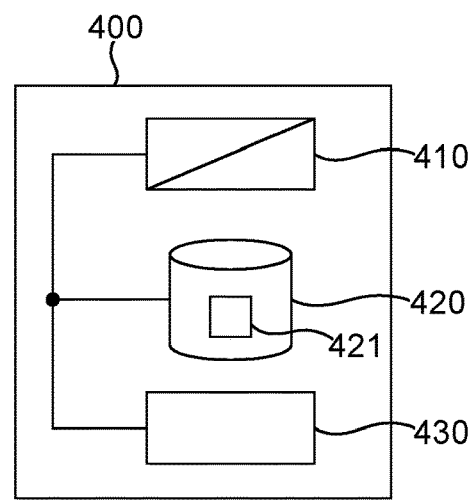
FIG. 4 is a block diagram of a treatment planning system according to an embodiment.

The method 300 may be implemented in a treatment planning system 400 of the type illustrated in FIG. 4. The treatment planning system may include an interface 410, a memory 420 and processing circuitry 430. The interface 410 is configured to receive, via a text or graphical user interface, a script or by data transfer, one or more non-photon radiation contributions $D^{(i)}(T,E)$, $1 \leq i \leq N$, dynamic assignments $\Pi$ of the combination in terms of non-negative coefficients $k_1, k_2, \ldots, k_N \geq 0$ and possible further data. The interface 410 may connect the treatment planning system 400 to a data network (not shown), so as to enable communication with users, clinicians, researchers, treatment planning personnel, radiation delivery systems etc. The memory 420 may be configured to store a computer program 421 with instructions for causing the treatment planning system 400 to carry out the method 300. The processing circuitry 430 may execute the instructions of the computer program 421, in particular to carry out the steps to be described in the next paragraphs.

In a first step 310 of the method 300, one or more non-photon radiation contributions $D^{(i)}(T,E)$, $1 \leq i \leq N$, are obtained. An $i^{th}$ one of the contributions may be represented as a list, table or matrix, which provides a value of the dose $D^{(i)}(T,E)$ at a location x for a pair of a particle type T and particle energy E. The location x may refer to a point, voxel or other region and will be implicit in the notation herein. The representation of the dose may be discrete or continuous with respect to the particle energy E. Each contribution may correspond to a beam or spot to be delivered in radiation therapy. Alternatively, each contribution may correspond to a preliminary treatment plan, such as a base plan or Pareto-optimal plan. It may not be explicit from a particular treatment plan how large physical dose will be absorbed in a particular volume of the patient when the treatment plan is carried out. If the treatment plan is not expressed in terms of physical dose, but rather in terms of, say, machine-level instructions, relatively complex computations may be required to determine or estimate the physical dose.

In an optional second step 312, a total dose $D_{tot}^{(i)} = \Sigma_{T,E} D^{(i)}(T,E)$ of each contribution is stored for later use in the method 300. The notation $\Sigma_{T,E} \ldots$ is shorthand for summing over all (T,E) pairs for which the dose $D^{(i)}(T,E) > 0$. If step 312 is not performed separately, the total dose of the contribution can be computed at a later stage.

In a likewise optional third step 314, a per-contribution dose-weighted average at least one biological effect multiplier is computed. The computation may be in accordance with the following equation:

$$\left(\bar{\delta}^{(i)}\right)^{1/p} = \frac{\sum_{T,E}(\delta(T,E))^{1/p} D^{(i)}(T,E)}{D_{tot}^{(i)}}, \quad 1 \leq i \leq N,$$

where p is the characteristic power of the biological effect multiplier and $$D_{tot}^{(i)} = \sum_{T,E} D^{(i)}(T,E)$$

is a total dose of the $i^{th}$ contribution. The above expression can be classified as a power mean with exponent p. For the Krämer & Scholz model discussed above, and bearing in mind the respective characteristic powers of the multipliers, this step 314 would include computing:

$$\bar{\alpha}^{(i)} = \frac{\sum_{T,E} \alpha(T,E) D^{(i)}(T,E)}{D_{tot}^{(i)}}, \quad 1 \leq i \leq N,$$

-continued $$\bar{\beta}^{(i)} = \left(\frac{\sum_{T,E} \sqrt{\beta(T,E)} D^{(i)}(T,E)}{D_{tot}^{(i)}}\right)^2, \quad 1 \leq i \leq N.$$

Since this operation may be at least partly performed by a different entity, e.g. by having $\delta(T,E)$ or $\delta(T,E)^{1/p} D^{(i)}(T,E)$ computed by external software in the manner explained above, step 314 is optional in the method 300.

In a next step 316, the per-contribution dose-weighted averages $\bar{\delta}^{(i)}$, $1 \leq i \leq N$, of the at least one biological effect multiplier with respect to each of the N contributions are stored. The storing may for example be performed in the memory 420 of the treatment planning system 400.

In a subsequent step 318 of the method 300, an assignment $\Pi$ of the combination of the N contributions is obtained. The assignment $\Pi$ may be in terms of non-negative coefficients $k_1, k_2, \ldots, k_N \geq 0$ to be applied to the N contributions. The assignment $\Pi$ may be obtained by setting the interface 410 in a mode where it is ready to accept input of the coefficients $k_1, k_2, \ldots, k_N$ from a user or another processor. Alternatively, the assignment $\Pi$ may be obtained by polling a memory space where they are to be found. In FIG. 3, the block 318 has one right-hand exit, representing no input of coefficients, in which case the execution of the method 300 loops back. The downward exit from block 318, representing that coefficients have been obtained, continues into the subsequent step 320 of determining a biological effect of the combination according to this assignment $\Pi$, denoted $-\ln S^{\Pi}$. After completion of step 320, the execution of the method 300 may loop back to block 318 to receive a new assignment $\Pi'$.

It is noted that a first set of coefficients $k_1, k_2, \ldots, k_N$ may sum to one, $$\sum_{i=1}^{N} k_i = 1,$$

and thereby define a convex combination $$\Pi = \sum_{i=1}^{N} k_i P_i$$

of base plans $P_1, P_2, \ldots, P_N$. The convex combination may be referred to as a navigated plan $\Pi$. A user may select the coefficients and inspect the resulting properties of the navigated plan using a navigation interface of the type described in the applicant's disclosure EP3581241A1. The navigation interface may include display means for displaying a list of clinical goals and an associated value range for each clinical goal, and a user input means enabling a user to input navigation weights. For each clinical goal, there is also preferably an indicator of whether the clinical goal is fulfilled. A set of altered coefficients $k_1', k_2', \ldots, k_N'$ may be obtained as a result of the user's continued navigation. The present way of computing the biological effect allows the user to receive responsive feedback with minimal latency when biological effect is one of the clinical goals.

Step 320 more precisely includes computing a combined dose-weighted average $\bar{\delta}^{\Pi}$ of said at least one biological effect multiplier on the basis of the stored per-contribution dose-weighted averages $\bar{\delta}^{(i)}$. The combined dose-weighted average is given by $$(\bar{\delta}^\Pi)^{1/p} = \frac{1}{D_{\Pi,tot}} \sum_{T,E} (\delta(T,E))^{1/p} D_\Pi(T,E) = \frac{1}{D_{\Pi,tot}} \sum_{T,E} \sum_{i=1}^{N} (\delta(T,E))^{1/p} k_i D^{(i)}(T,E) =$$

$$\frac{1}{D_{\Pi,tot}} \sum_{i=1}^{N} k_i \sum_{T,E} (\delta(T,E))^{1/p} D^{(i)}(T,E) = \frac{1}{D_{\Pi,tot}} \sum_{i=1}^{N} k_i (\bar{\delta}^{(i)})^{1/p} D^{(i)}_{tot}.$$

If the RBE model comprises no other biological effect multiplier than $\delta(T,E)$, the biological effect is given as the product of $\bar{\delta}^\Pi$ and the $p^{th}$ power of the total dose $D_{\Pi,tot}$ of the combination $\Pi$, as follows:

$$-\ln S^\Pi = \bar{\delta}^\Pi D_{\Pi,tot}^2 = \left( \sum_{i=1}^{N} k_i (\bar{\delta}^{(i)})^{1/p} D^{(i)}_{tot} \right)^p.$$

See Zaider and Rossi, "The synergistic effects of different radiations", *Radiat. Res.* (1980), vol. 83, pp. 732-739 [doi: 10.2307/3575352]. As the inventors have realized, the per-contribution dose-weighted averages $\bar{\delta}^{(i)}$ and the total per-contribution doses $D_{tot}^{(i)}$ are independent of the coefficients $k_1, k_2, \ldots, k_N$. Therefore, when a new assignment $\Pi'$ of the combination is obtained in an iteration of step 318 (e.g., by obtaining new coefficient values $k_1', k_2', \ldots, k_N'$), its biological effect $-\ln S^{\Pi'}$ can be computed by substituting $k_i \mapsto k_i'$ in the above expression. There is no need to recompute $\bar{\delta}^{(i)}$ or tot. The biological effect $-\ln S^\Pi$ or new biological effect $-\ln S^{\Pi'}$ may be used to support radiation treatment planning.

For an RBE model with two or more biological effect multipliers, the equivalent-dose contributions are summed. In the particular case of the Krämer & Scholtz model discussed above, such summing yields:

$$-\ln S^\Pi = \sum_{T,E} \left( \beta(T,E) D(T,E)^2 + \alpha(T,E) D(T,E) \right) =$$

$$\bar{\beta}_\Pi D^2_{\Pi,tot} + \bar{\alpha}_\Pi D_{\Pi,tot} = \left( \sum_{i=1}^{N} k_i \sqrt{\bar{\beta}^{(i)}} D^{(i)}_{tot} \right)^2 + \sum_{i=1}^{N} k_i \bar{\alpha}^{(i)} D^{(i)}_{tot}.$$

As seen above, the combination provides, for each assignment $\Pi$, a mixed radiation field whose total biological effect is obtained by summing the contributions to $-\ln S^\Pi$ over all $(T,E)$ pairs for which there is a non-zero dose. The calculations are structured in the manner presented above to enable a computationally efficient refresh when the coefficients $k_1, k_2, \ldots, k_N$ are altered.

Figure 1:
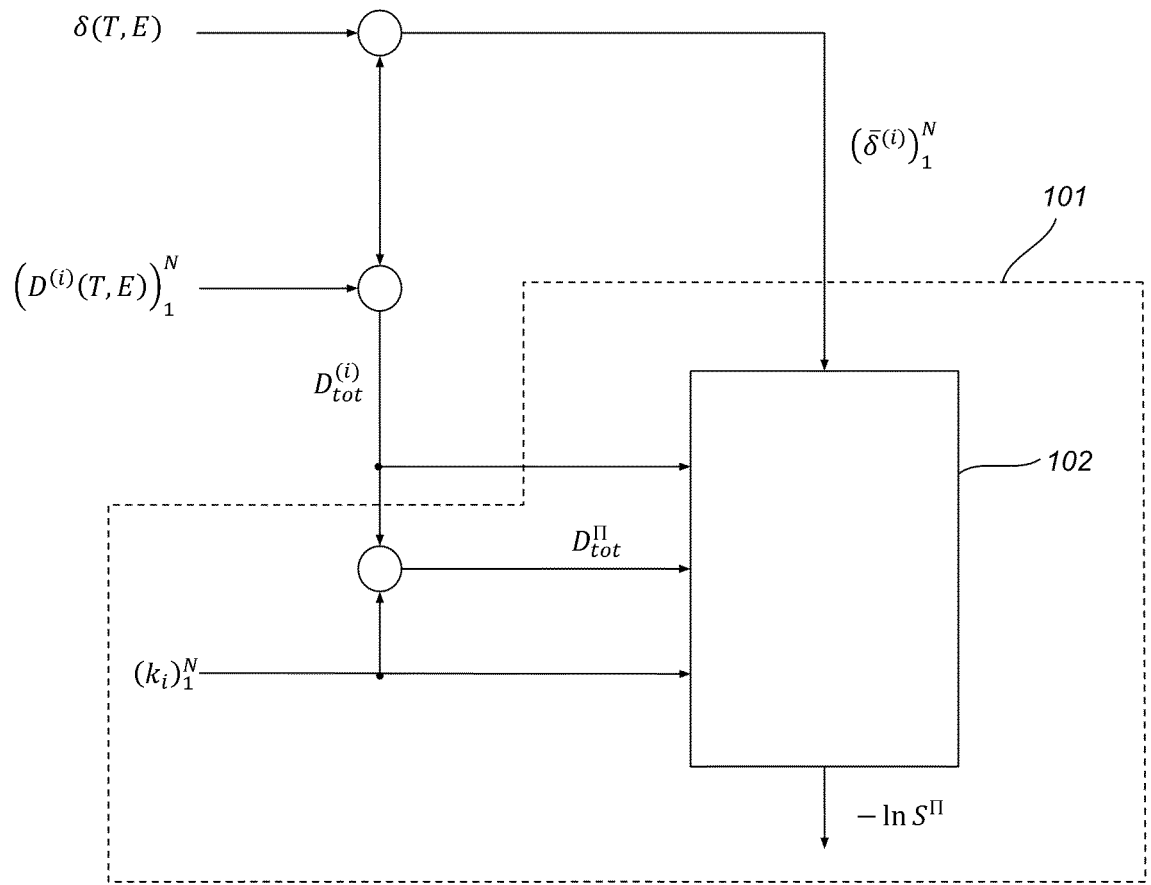
FIG. 1 illustrates schematically how the dynamic computation of biological effect $-\ln S^{\Pi}$ is organized according to embodiments of the invention.

The computational structure is visualized in FIG. 1, where input quantities $\delta(T,E)$, $(D^{(i)}(T,E))_1^N$, and $(k_i)_1^N$ are shown at the left-hand size. The notation shall be understood in the sense that $(f(i))_1^N = \{f(1), f(2), \ldots, f(N)\}$. The intermediate quantities $\bar{\delta}^{(i)}$ and $D_{tot}^{(i)}$, which can be calculated without knowledge of $(k_i)_1^N$ are shown outside the area 101. The intermediate quantity $$D_{\Pi,tot} = \sum_{i=1}^{N} k_i D^{(i)}_{tot}$$

is shown inside this area 101. The total biological effect $-\ln S^\Pi$ is calculated by a function illustrated by the block 102 on the basis of the three intermediate quantities and the coefficients $(k_i)_1^N$.

Figure 2:
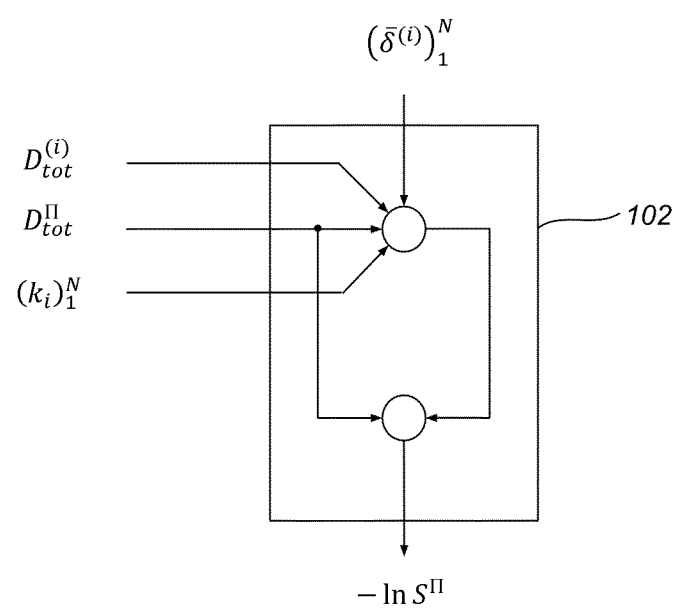
FIG. 2 is a detail of FIG. 1.

FIG. 2 shows the inner workings of the block 102, which reveals that the total biological effect $-\ln S^\Pi$ is calculated in two steps. Initially the combined dose-weighted average $\bar{\delta}^\Pi$ of each biological effect multiplier is computed. Then, the combined dose-weighted average $\bar{\delta}^\Pi$ is multiplied by the $p^{th}$ power of the total dose $D_{\Pi,tot}$ and output as $-\ln S^\Pi$.

An advantage of embodiments of disclosed herein is that only the computations inside the area 101, which represent a relatively limited effort, need to be repeated when a new set of coefficients $k_1', k_2', \ldots, k_N'$ is received.

The computational structure of FIG. 1 may provide benefit also in the case of a scaling of a treatment plan. The treatment plan to be scaled can then be regarded as a base plan $P_1$ constituting the sole contribution $N=1$, and its coefficient $k_1$ will be the scaling factor. Accordingly, the total dose is $D_{\Pi,tot} = k_1 D_{tot}^{(1)}$, so that $\bar{\alpha}_\Pi = \bar{\alpha}^{(1)}$ and $\bar{\beta}_\Pi = \bar{\beta}^{(1)}$. The biological effect is given by:

$$-\ln S = \sum_{T,E} \left( \beta(T,E) D(T,E)^2 + \alpha(T,E) D(T,E) \right) =$$

$$\bar{\beta}_\Pi D^2_{\Pi,tot} + \bar{\alpha}_\Pi D_{\Pi,tot} = \bar{\beta}^{(1)} D^2_{\Pi,tot} + \bar{\alpha}^{(1)} D_{\Pi,tot},$$

where $\bar{\alpha}^{(1)}$, $\bar{\beta}^{(1)}$, the dose-weighted averages with respect to the base plan $P_1$, can be precalculated. The biological effect is a second-order polynomial in $k_1$.

The aspects of the present disclosure have mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A method for dynamically estimating a biological effect of a variable combination of non-photon radiation in accordance with a relative biological effectiveness, RBE, model including at least one biological effect multiplier $\delta(T,E)$ which depends on particle type T and/or particle energy E, such that its contribution to the biological effect is $\delta(T,E) D(T,E)^p$, where $p>0$ is a characteristic power of the biological effect multiplier, the method comprising:

obtaining one or more non-photon radiation contributions $D^{(i)}(T,E)$, $1 \leq i \leq N$, at least one of said contributions including multiple particle types and/or multiple particle energies;

storing per-contribution dose-weighted averages $\bar{\delta}^{(i)}$, $1 \leq i \leq N$, of said at least one biological effect multiplier with respect to each of the one or more contributions; and in response to obtaining an assignment $\Pi$ of the combination, the assignment being in terms of non-negative coefficients $k_1, k_2, \ldots, k_N \geq 0$ to be applied to the one or more contributions, determining a biological effect of the combination, including computing a combined dose-weighted average $\bar{\delta}^\Pi$ of said at least one biological effect multiplier on the basis of the stored per-contribution dose-weighted averages.

2. The method of claim 1, wherein the combined dose-weighted average $\bar{\delta}^\Pi$ of said at least one biological effect multiplier is computed as a power mean with exponent $1/p$ of each stored per-contribution dose-weighted average $\bar{\delta}^{(i)}$ weighted by the respective coefficient $k_i$ and a total dose $D_{tot}^{(i)} = \sum_{T,E} D^{(i)}(T,E)$ of that contribution:

$$\left(\bar{\delta}^{\Pi}\right)^{1/p} = \frac{\sum_i \left(\bar{\delta}^{(i)}\right)^{1/p} k_i D_{tot}^{(i)}}{\sum_i k_i D_{tot}^{(i)}},$$

where p>0 is the characteristic power of the biological effect multiplier.

3. The method of claim 1, wherein determining the biological effect of the combination includes multiplying a $p^{th}$ power of the total dose $D_{tot}^{\Pi}$ of the combination $\Pi$ with the combined dose-weighted average $\bar{\delta}^{\Pi}$ of said at least one biological effect multiplier.

4. The method of claim 1, further comprising storing a total dose $D_{tot}^{(i)} = \Sigma_{T,E} D^{(i)}(T,E)$ of the contribution for use in the determination of the biological effect of the combination $\Pi$.

5. The method of claim 1, further comprising computing the per-contribution dose-weighted average of the at least one biological effect multiplier using the equation:

$$\left(\bar{\delta}^{(i)}\right)^{1/p} = \frac{\sum_{T,E} (\delta(T,E))^{1/p} D^{(i)}(T,E)}{D_{tot}^{(i)}}, 1 \le i \le N,$$

where p>0 is a characteristic power of the biological effect multiplier and $D_{tot}^{(i)} = \Sigma_{T,E} D^{(i)}(T,E)$ is a total dose of the $i^{th}$ contribution.

6. The method of claim 1, wherein p=1 for at least one biological effect multiplier $\delta(T,E)$ of the RBE model.

7. The method of claim 6, wherein the at least one biological effect multiplier includes an α multiplier of a linear quadratic model, such as an $\alpha_0$ term or $z_{1D}^*$ term of a microdosimetric-kinetic model, MKM.

8. The method of claim 1, wherein p=2 for at least one biological effect multiplier $\delta(T,E)$ of the RBE model.

9. The method of claim 8, wherein the at least one biological effect multiplier includes a β multiplier of a linear-quadratic model.

10. The method of claim 1, wherein each contribution represents a beam or spot to be delivered in radiation therapy.

11. The method of claim 1, wherein each contribution represents a radiation treatment plan, such as a base plan or Pareto-optimal plan.

12. The method of claim 11, wherein the coefficients represent a convex combination of the contributions.

13. The method of claim 12, wherein the contributions represent base plans obtained by multi-criteria optimization, MCO, and the combination corresponds to a navigated plan.

14. The method of claim 1, wherein the combination corresponds to a scaling of a radiation treatment plan.

15. The method according to claim 1, wherein the non-photon radiation includes proton radiation, helium ions or carbon ions.

16. The method of claim 1, further comprising using the determined biological effect of the combination to support radiation treatment planning.

17. A treatment planning system configured to dynamically estimate a biological effect of a variable combination of non-photon radiation in accordance with a relative biological effectiveness, RBE, model including at least one biological effect multiplier $\delta(T,E)$ which depends on particle type T and/or particle energy E, such that its contribution to the biological effect is $\delta(T,E) D(T,E)^p$, where p>0 is a characteristic power of the biological effect multiplier, the system comprising:
  an interface configured to receive
    one or more non-photon radiation contributions $D^{(i)}(T, E)$, 1≤i≤N, at least one of said contributions including multiple particle types and/or multiple particle energies, and
    dynamic assignments Π of the combination, the assignments being in terms of non-negative coefficients $k_1$, $k_2$, ..., $k_N \ge 0$ to be applied to the one or more contributions;
  a memory configured to store per-contribution dose-weighted averages $\bar{\delta}^{(i)}$, 1≤i≤N, of said at least one biological effect multiplier with respect to each of the one or more contributions; and
  processing circuitry configured to determine, for each received dynamic assignment Π of the combination, a biological effect of the combination, including computing a combined dose-weighted average $\bar{\delta}^{\Pi}$ of said at least one biological effect multiplier on the basis of the stored per-contribution dose-weighted averages.

18. A computer program product, comprising a non-transitory storage medium containing instructions which, when executed by a computer, cause a computer to carry out the method of claim 1.

* * * * *